US008710274B2

(12) United States Patent
Pourreau et al.

(10) Patent No.: US 8,710,274 B2
(45) Date of Patent: Apr. 29, 2014

(54) METHOD OF PURIFYING CRUDE ACETONE STREAM

(75) Inventors: Daniel B Pourreau, Exton, PA (US); Roger A Grey, West Chester, PA (US); Andrew P Kahn, Eagleville, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 31 days.

(21) Appl. No.: 13/464,726

(22) Filed: May 4, 2012

(65) Prior Publication Data

US 2013/0296612 A1 Nov. 7, 2013

(51) Int. Cl.
C07C 45/83 (2006.01)
C07C 29/84 (2006.01)
C07C 29/145 (2006.01)

(52) U.S. Cl.
USPC .......................... 568/410; 568/411; 568/881

(58) Field of Classification Search
USPC .......................................... 568/410, 411, 881
See application file for complete search history.

(56) References Cited

U.S. PATENT DOCUMENTS

| 2,238,016 | A | 4/1941 | Downey et al. |
| 2,906,676 | A | 9/1959 | Bewley et al. |
| 3,330,741 | A | 7/1967 | Theilig et al. |
| 3,409,513 | A | 11/1968 | Hamlin et al. |
| 3,531,376 | A | 9/1970 | Minoda et al. |
| 3,668,256 | A | 6/1972 | Brundege et al. |
| 4,219,507 | A | 8/1980 | Miki et al. |
| 4,336,109 | A | 6/1982 | Hosaka et al. |
| 4,584,063 | A | 4/1986 | Berg et al. |
| 4,722,769 | A | 2/1988 | Chan et al. |
| 4,766,249 | A | 8/1988 | Buck et al. |
| 4,778,882 | A | 10/1988 | Oka et al. |
| 4,931,145 | A | 6/1990 | Berg et al. |
| 5,057,192 | A | 10/1991 | Zoeller et al. |
| 5,240,566 | A | 8/1993 | Hahn et al. |
| 5,399,776 | A | 3/1995 | Fraini et al. |
| 5,567,853 | A | 10/1996 | Gupta et al. |
| 5,762,764 | A | 6/1998 | Chang et al. |
| 5,788,818 | A | 8/1998 | Lorenzoni et al. |
| 6,303,826 | B1 | 10/2001 | Bhinde et al. |
| 6,331,654 | B1 | 12/2001 | Zakoshansky et al. |
| 6,340,777 | B1 | 1/2002 | Aristovich et al. |
| 6,657,087 | B2 | 12/2003 | Weber et al. |
| 6,762,328 | B2 | 7/2004 | Saayman et al. |
| 7,041,857 | B1 | 5/2006 | Hayes et al. |
| 7,282,613 | B2 | 10/2007 | Black et al. |
| 7,416,645 | B2 | 8/2008 | Weber et al. |
| 7,605,291 | B2 | 10/2009 | Maldonado et al. |
| 8,030,525 | B2 | 10/2011 | Nelson et al. |
| 8,058,479 | B2 | 11/2011 | Nelson et al. |

FOREIGN PATENT DOCUMENTS

| EP | 82349 | 12/1984 |
| EP | 242555 | 5/1992 |
| EP | 40985 | 7/1993 |
| EP | 767160 | 4/1997 |
| EP | 1226102 | 10/2006 |
| EP | 1380561 | 3/2008 |
| WO | 9712654 | 4/1997 |
| WO | 0130735 | 5/2001 |
| WO | 0153242 | 7/2001 |
| WO | 2010077724 | 7/2010 |
| WO | 2010077725 | 7/2010 |
| WO | 2010079317 | 7/2010 |

OTHER PUBLICATIONS

PCT International Search Report and The Written Opinion—Mailed Sep. 25, 2013 for Corresponding PCTUS2013/039039.

*Primary Examiner* — Sikarl Witherspoon

(57) ABSTRACT

The present invention relates to a method of treating a crude acetone stream. The method generally includes treating a crude acetone stream which has acetone and at least one low-boiling impurity with a catalyst to form a treated acetone stream that has acetone and at least one higher-boiling impurity and then distilling the treated acetone stream to remove at least a portion of the higher-boiling impurity to produce a purified acetone stream. This is particularly helpful in processes where a more pure acetone is desired, including a process for making purified isopropanol.

19 Claims, No Drawings

METHOD OF PURIFYING CRUDE ACETONE STREAM

BACKGROUND

The present invention relates to a method of treating a crude acetone stream. The invention relates to a method of purifying a crude acetone stream so as to convert low boiling impurities to higher boiling impurities that can be more easily separated from the acetone. This is particularly helpful in processes where a more pure acetone is desired, including a process for making highly purified isopropanol.

SUMMARY OF THE INVENTION

The present invention relates to a method of treating a crude acetone stream. This invention relates to a method of purifying a crude acetone stream so as to convert low boiling impurities to higher boiling impurities that can be more easily separated from acetone. This is particularly helpful in processes where a more pure acetone is desired, including a process for making purified isopropanol.

In some embodiments, the present invention provides a method of purifying a crude acetone stream which comprises treating a crude acetone stream which comprises acetone and at least one low-boiling impurity with a solid acid catalyst to form a treated acetone stream that comprises acetone and at least one higher-boiling impurity and then distilling the treated acetone stream to remove at least a portion of the higher-boiling impurity to produce a purified acetone stream.

In other embodiments, the present invention provides a method for preparing a purified isopropanol comprising the steps of feeding an acetone stream which comprises acetone and at least one lower boiling impurity to a solid inorganic acid bed which comprises a catalyst to form a treated acetone stream that comprises acetone and at least one higher boiling impurity; distilling the treated acetone stream to remove at least a portion of the higher boiling impurity from the treated acetone stream to produce a purified acetone stream; and feeding the purified acetone stream to a hydrogenation reactor in a process for making isopropanol to produce purified isopropanol.

In other embodiments, the present invention provides a method for preparing a purified isopropanol comprising the steps of feeding an acetone stream which comprises acetone and at least one lower boiling impurity to a solid inorganic acid bed which comprises a zeolite catalyst to form a treated acetone stream that comprises acetone and at least one higher boiling impurity; distilling the treated acetone stream to remove at least a portion of the higher boiling impurity from the treated acetone stream to produce a purified acetone stream having a purity of at least 80%; feeding the purified acetone stream to a hydrogenation reactor in a process for making isopropanol to produce a crude isopropanol; distilling the crude isopropanol to produce a purified isopropanol wherein the purified isopropanol has a purity of at least 99.5%.

The features and advantages of the present invention will be readily apparent to those skilled in the art upon a reading of the description of the preferred embodiments that follows.

DETAILED DESCRIPTION

The present invention relates to a method of treating a crude acetone stream. This invention relates to a method of purifying a crude acetone stream so as to convert low boiling impurities to higher boiling impurities that can be more easily separated from acetone. This is particularly helpful in processes where a more pure acetone is desired, including a process for making purified isopropanol.

The present invention provides methods of treating crude acetone streams so that some of the lower boiling impurities are converted to higher boiling impurities. This facilitates the removal of impurities from the acetone stream, as separation of higher boiling impurities is easier, less costly, and more effective than removal of lower boiling impurities from acetone.

In some embodiments, the present invention provides a method of purifying a crude acetone stream which comprises treating a crude acetone stream which comprises acetone and at least one low-boiling impurity with a solid acid catalyst to form a treated acetone stream that comprises acetone and at least one higher-boiling impurity and then distilling the treated acetone stream to remove at least a portion of the higher-boiling impurity to produce a purified acetone stream.

In other embodiments, the present invention provides a method for preparing a purified isopropanol comprising the steps of feeding an acetone stream which comprises acetone and at least one impurity to a solid inorganic acid bed which comprises a catalyst to form a treated acetone stream that comprises acetone and at least one higher boiling impurity then distilling the treated acetone stream to remove at least a portion of the higher boiling impurity from the treated acetone stream to produce a purified acetone stream, and then feeding the purified acetone stream to a hydrogenation reactor in a process for making isopropanol to produce a purified isopropanol.

In other embodiments, the present invention provides a method for preparing a purified isopropanol comprising the steps of feeding an acetone feed stream which comprises acetone and at least one lower boiling impurity to a solid inorganic acid bed which comprises a zeolite catalyst to form a treated acetone stream that comprises acetone and at least one higher boiling impurity; distilling the treated acetone stream to remove at least a portion of the higher boiling impurity from the treated acetone stream to produce a purified acetone stream having a purity of at least 80%; feeding the purified acetone stream to a hydrogenation reactor in a process for making isopropanol to produce a purified isopropanol; wherein the purified isopropanol has a purity of at least 99.5%. A further embodiment provides the use of a dual resin bed and dryer configuration.

Lower boiling impurities that can be found in crude acetone streams generally include: alcohols, esters, ethers, epoxides, aldehydes, water, and olefins. In some embodiments, the lower boiling impurities can include isobutylene, acetaldehyde, methanol, methyl formate, isopropanol, propionaldehyde, tert-butyl alcohol, isobutanol, methyl tert-butyl ether ("MTBE"), isobutyraldehyde, methyl ethyl ketone, t-butyl formate, propylene and isobutylene oxides, and diisobutylene. Generally any impurity which has a boiling point similar to acetone or form azeotropes with acetone, such that it is difficult to separate from acetone via distillation, would be considered a lower boiling impurity.

Higher boiling impurities that can be formed from the lower boiling impurities in crude acetone streams generally include ethers, alkyl acetals, alcohols, glycol ethers, dioxolanes, glycols, and ketones. In some embodiments, the higher boiling impurities can include 1,1-dimethoxypropane, 2,2-dimethoxypropane, 1-methoxy-2-methyl-2-propanol, 2,4,4-trimethoxydioxolane, 1,1-dimethoxyisobutane, 2,2,4,4-tetramethyldioxolane, 2-methoxy-2-methyl-1-propanol, 2-isobutyl-4,4-dimethyl-dioxolane, mesityl oxide, hydroxymesityl oxide, methoxymesityl oxide, propylene glycol ethers, propylene glycol and isobutylene glycol. Generally any impurity which has a higher boiling point than acetone, and thus are more easily separated from acetone via distillation, would be considered a higher boiling impurity.

Catalysts that can be used to treat the crude acetone stream include: zeolites, including delaminated zeolites, mesoporous silicas, acid clays, mixed inorganic oxides, acidic inorganic oxides, crosslinked acidic polymer resins, or mixtures thereof.

Examples of zeolites include silicate-based zeolites and amorphous compounds such as faujasite, mordenite, chabazite, offretite, clinoptilolite, erionite, sihealite, and the like. Other suitable zeolite materials include zeolite A, zeolite L, zeolite beta, zeolite X, zeolite Y, zeolite HY, ZSM-5, MCM-22, MCM-41, UCB-1, and ITQ-2. A preferred zeolite catalyst is an HY zeolite that has a silica to alumina ratio between 2 and 10. The zeolite can be of any formed shape including extrudates, tablets, formed particles or beads. The use of binders to provide strength to the formed shape can be used. A particularly preferred zeolite catalyst is an 80/20 composition of Zeolite HY and alumina binder in extrudate form. It has been found that this particular composition gives the catalyst mechanical integrity in fixed bed operation and minimizes reactor pressure drop and plugging.

Zeolites are commonly altered through a variety of methods to adjust characteristics such as pore size, structure, activity, acidity, and silica/alumina molar ratio. The silica/alumina ratio of the zeolite can be altered, via a variety of methods, such as dealumination by steaming or acid washing to increase the silica/alumina ratio. Increasing the amount of silica relative to alumina can have the effect of increasing the catalyst hydrophobicity. The silica/alumina ratio can range from less than 0:5 to 500 or greater.

Examples of acidic inorganic oxides include, but are not limited to, acid treated clays, aluminas, silica-aluminas, silica containing mixed oxides, natural and synthetic pillared clays, and natural and synthetic zeolites. Examples of silica containing mixed oxides include silica-titania, silica-zirconia, silica-alumina-titania and silica-alumina-zirconia.

Examples of acid treated clays include montmorillonite clays, and smectite clays.

Examples of crosslinked acidic polymer resins include, but are not limited to divinylbenzene-crosslinked sulfonated polystyrene resins, sulfonated tetrafluoroethylene based fluoropolymer-copolymers, and the like. A particularly preferred crosslinked acidic polymer resin is a divinylbenzene-crosslinked sulfonated polystyrene resin. It should be noted that swelling can occur with at least some organic solid acids, such as Amberlyst 15. Preferred organic solid acids would not be subject to swelling.

The described methods are particularly helpful in processes where a more pure acetone is desired. Examples of such processes include a process for making solvent-grade isopropanol, solvent grade acetone, acetone cyanohydrin/methyl methacrylate, bisphenol A, methyl isobutyl ketone, methyl isobutyl carbinol, and isophorone.

The crude acetone streams of the present invention can vary. In some embodiments, the crude acetone stream may be at least 50% acetone, at least 60% acetone, at least 70% acetone, or at least 80%.

The purified acetone streams of the present invention will vary based on the crude acetone stream, the catalyst selected, and other variables. In some embodiments, the purified acetone stream will be at least 80% acetone. In preferred embodiments, the purified acetone stream will be at least 90% acetone.

In some embodiments, once a purified acetone stream is obtained, the purified acetone stream is hydrogenated to produce a crude isopropanol stream. In such embodiments, the yield of isopropanol is increased when compared to methods that do not use the process of purifying the acetone stream. In preferred embodiments, the yield of isopropanol is increased by at least 10% when compared to a process of producing isopropanol with an acetone fed stream that has not been fed to a solid inorganic acid bed.

Additionally, in some embodiments, the crude isopropanol stream is further purified to produce purified isopropanol. The crude isopropanol stream can be further purified using methods well known in the art, such as distillation, extractive distillation, or reactive distillation. In preferred embodiments the purified isopropanol stream has a purity of at least 99.0%. In other preferred embodiments, the purified isopropanol stream has a purity of at least 99.5%. In the most preferred embodiment, the purified isopropanol stream has a purity of at least 99.8%.

One exemplary embodiment involves the production of isopropanol. In the production of isopropanol, crude acetone is then converted to isopropanol by hydrogenation. Both the crude acetone stream and the isopropanol are purified by distillation. In this particular embodiment, a fixed bed containing acid catalyst is positioned between the crude acetone source and the first distillation column. The acid bed causes the lower boiling impurities in the crude acetone to react with alcohols or and water or to isomerize to the corresponding aldehydes that further react with contained alcohols to produce higher boiling impurities, such as glycols, glycol ethers, acetals, diacetals, and dioxolanes that are removed from the bottoms of the first distillation column. In preferred embodiments, about twenty percent of the methanol and substantially all of the epoxides and aldehydes are removed from the acetone stream that enters the hydrogenation reactor in the process for production of isopropanol. This reduces the amount of t-butyl alcohol, sec-butanol, ethanol, and methanol by-products that exit the reactor. Because the contaminants are reduced, the isopropanol is more easily purified via distillation. The production rates are increased and higher product purity is also achieved. In preferred embodiments, the resulting product is 99.0% pure isopropanol. In other embodiments, the resulting isopropanol is up to or greater than 99.8% pure.

In further preferred embodiment involving the production of isopropanol, a drying medium is added before the organic acid resin bed to remove water from the crude acetone. The acid resin catalyst can be purchased in its dry form or the wet form pre-dried by known means, such as by passing hot nitrogen over the resin bed. A particularly preferred drying medium is 3A zeolite beads, which are microporous aluminosilicates with average pore diameter of 3 Angstrom. Using such 3A Zeolite beads can reduce the water content of the crude acetone stream by up to 96%. By reducing the water content, it is expected that the amount of t-butyl alcohol formed on the acid resin bed will be reduced and thus result in a higher yield of high purity isopropanol product. In addition, it is expected that more isobutylene will be converted to di-isobutylene and MTBE instead of t-butyl alcohol. Di-isobutylene can be efficiently removed with the bottoms of the first acetone distillation column and MTBE can be removed with the lights in the first isopropanol distillation column.

In an embodiment, a dual resin bed and dryer configuration can be used. The dual resin bed and dryer configuration can be used in processes which require purification of an acetone crude stream, including processes such as processes for making solvent-grade isopropanol, solvent grade acetone, acetone cyanohydrin/methyl methacrylate, bisphenol A, methyl isobutyl ketone, methyl isobutyl carbinol, and isophorone. Use of a dual resin bed and dryer configuration would allow a zeolite and resin bed to be taken out of service or reactivated in-situ using known methods, such as with hot air or nitrogen while the crude acetone processing continues. This would also allow the used Zeolite and/or resin bed to be replaced, reactivated, or maintenance to be conducted without interrupting the production of isopropanol. Waste water stream from drying of the catalyst and zeolite beds could be sent to waste fuel tanks or a waste water treatment facility, or disposed of or recycled in other known manners.

Various parameters will be understood by one of skill in the art as affecting the method of treating a crude acetone stream. Such parameters will include temperature of the reaction, WHSV, and catalyst bed length to reactor diameter L/D ratio. In some embodiments, the temperature will range from about 30° C. about 70° C. In other embodiments, it will range from about 40° C. to about 60° C. In most preferred embodiments it will be about 50° C. In some embodiments, the weight hourly space velocity ("WHSV") will range from about 0.3 to about 2.5 $hr^{-1}$. In other embodiments, it will range from about 0.5 to about 2.0 $hr^{-3}$. In most preferred embodiments it will be about 1.0 $hr^{-1}$. In some embodiments, the catalyst bed length to reactor diameter L/D ratio will range from about 1 to about 30. In other embodiments, it will range from about 2 to about 8. In some embodiments it will be about 6. In other embodiments, it will be about 2. The various parameters can be manipulated by a person of skill in the art so as to produce optimal working conditions.

To facilitate a better understanding of the present invention, the following examples of preferred embodiments are given. In no way should the following examples be read to limit, or to define, the scope of the invention.

EXAMPLES

For Examples 1-11, a 1 inch ID jacketed tube was charged with solid acid catalyst. The tube was heated to 50° C. and the crude acetone (75 wt % acetone, 8 wt % methanol (MeOH), 3.5 wt % isobutylene oxide (IBO), 1.2 wt % propylene oxide (PO), 0.2 wt % acetaldehyde (AcH), 0.2% propionaldehyde (PA), 0.6 wt % isobutyraldehyde (IBA), balance=other organic compounds) was fed to the column at 50 g/h (WHSV=1/h). Samples were collected and analyzed by gas chromatography.

For Examples 12-16, a ¾ inch OD stainless steel tube was charged with catalyst. The tube was heated to 50° C. by placing it in a heated bath and the crude acetone (76.2 wt % acetone, 6.8 wt % methanol (MeOH), 3.7 wt % isobutylene oxide (IBO), 1.6 wt % propylene oxide (PO), 0.2 wt % acetaldehyde (AcH), 0.3% propionaldehyde (PA), 0.7 wt % isobutyraldehyde (IBA), balance=other organic compounds) was fed to the reactor. For Amberlyst 15 (Rohm & Haas), WHSV is expressed on a dry resin basis assuming 50% by weight water. In the cases where a pre-bed was used, 50 g of 3 A sieves (Aldrich, 8/12 mesh) were packed into a ¾' OD stainless steel tube placed in series before the main reactor. Samples were collected and analyzed by gas chromatography. A summary of the results are shown in the table below:

TABLE 1

| % Conversion to Heavier Compounds | | | | |
|---|---|---|---|---|
| | Ex 1 HY Zeolyst CBV600 SiO2/Al2O3 = 5.2 | Ex 2 HBeta Zeolyst CP 7146 SiO2/Al2O3 = 25 | Ex 3 HBeta Zeolyst CP 811E-300 SiO2/Al2O3 = 300 | Ex 4 Montmorillonite Clay BASF F24 |
| g cat | 50 | 50 | 50 | 50 |
| WHSV (h−1) | 1 | 1 | 1 | 1 |
| Temp (° C.) | 50 | 50 | 50 | 50 |
| Acetaldehyde | 85 | 88 | 88 | 88 |
| Propionaldehyde | 75 | 28 | 70 | 33 |
| Isobutyraldehyde | 60 | 62 | 68 | 72 |
| Propylene Oxide | 98 | 99 | 99 | 100 |
| Isobutylene Oxide | 100 | 100 | 100 | 100 |
| MeOH | 20 | 23 | 20 | 17 |
| Acetone | 2 | 4 | 4 | 2 |
| | Ex 5 ZSM5 Tricat | Ex 6 HY Zeolyst CBV400 SiO2/Al2O3 = 5.1 | Ex 7 HY Zeolyst CBV600 SiO2/Al2O3 = 5.2 | Ex 8 HY Zeolyst CBV600 SiO2/Al2O3 = 5.2 |
| g cat | 50 | 50 | 15 | 48 |
| WHSV (h−1) | 1 | 1 | 1 | 0.5 |
| Temp (° C.) | 50 | 50 | 70 | 50 |
| Acetaldehyde | 82 | 79 | 47 | 65 |
| Propionaldehyde | 65 | 65 | 46 | 75 |
| Isobutyraldehyde | 10 | 46 | 21 | 58 |
| Propylene Oxide | 97 | 92 | 75 | 97 |
| Isobutylene Oxide | 97 | 100 | 94 | 100 |
| MeOH | 17 | 20 | 13 | 19 |
| Acetone | 1 | 2 | 1 | 2 |
| | Ex 9 HY Zeolyst CBV600 SiO2/Al2O3 = 5.2 | Ex 10 HY Zeolyst CBV600 SiO2/Al2O3 = 5.2 | Ex 11 HY Zeolyst CBV600 SiO2/Al2O3 = 5.2 | Ex 12 Amberlyst 15 |
| g cat | 48 | 16 | 16 | 36 |
| WHSV (h−1) | 0.5 | 2 | 2 | 2.8 |

TABLE 1-continued

% Conversion to Heavier Compounds

| | | | | |
|---|---|---|---|---|
| Temp (° C.) | 30 | 50 | 30 | 50 |
| Acetaldehyde | 61 | 72 | 49 | 80 |
| Propionaldehyde | 70 | 57 | 41 | 69 |
| Isobutyraldehyde | 48 | 29 | 8 | 42 |
| Propylene Oxide | 75 | 75 | 74 | 99 |
| Isobutylene Oxide | 100 | 96 | 100 | 100 |
| MeOH | 22 | 19 | 14 | 19 |
| Acetone | 3 | 2 | 2 | 1 |

| | Ex 13 Prebed 3A sieve + Amberlyst 15 | Ex 14 Prebed 3A sieve + Amberlyst 15 | Ex 15 Prebed 3A sieve + HY Zeolyst CBV600 SiO2/Al2O3 = 5.2 | Ex 16 Prebed 3A sieve + Montmorillonite Clay BASF F24 |
|---|---|---|---|---|
| g cat | 36 | 36 | 22 | 31 |
| WHSV (h−1) | 2.8 | 5.6 | 2.3 | 1.6 |
| Temp (° C.) | 50 | 50 | 50 | 50 |
| Acetaldehyde | 83 | 81 | 81 | 94 |
| Propionaldehyde | 69 | 72 | 75 | 98 |
| Isobutyraldehyde | 24 | 32 | 45 | 77 |
| Propylene Oxide | 99 | 98 | 83 | 99 |
| Isobutylene Oxide | 100 | 100 | 97 | 100 |
| MeOH | 32 | 29 | 25 | 27 |
| Acetone | 1 | 1 | 2 | 4 |

As shown in the above Table 1, the low-boiling impurities are converted to higher-boiling impurities. For instance, the acetaldehyde content is reduced 47-88%, propionaldehyde is reduced by 75-99%, isobutyraldehyde is reduced by 28-75%, and isobutylene oxide is reduced by 94-100%.

The data shows that temperature can be manipulated to lead to more efficient removal of low-boiling impurities, with 50° C. being the preferred temperature. Additionally, a higher WHSV can lead to less acetone loss. One of skill in the art will understand that these factors can be manipulated to reduce acetone loss and increase the efficiency of removal of low-boiling impurities.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method of purifying a crude acetone stream which comprises
   a. treating a crude acetone stream which comprises acetone and at least one low-boiling impurity with a zeolite to form a treated acetone stream that comprises acetone and at least one higher-boiling impurity than in the crude acetone stream;
   b. distilling the treated acetone stream to remove at least a portion of the higher-boiling impurity to produce a purified acetone stream.

2. The method of claim 1 wherein the zeolite is selected from the group consisting of a faujasite, a mordenite, a chavbazite, a clinoptilolite, an erionite, a sihealite, a zeolite A, a zeolite L, a zeolite beta, a zeolite X, a zeolite Y, a zeolite HY, a zeolite ZSM-5, a zeolite MCM-22, a zeolite MCM-41, a zeolite UCB-1 and a zeolite ITQ-2.

3. The method of claim 2 wherein the zeolite is a zeolite ZSM-5.

4. The method of claim 2 wherein the zeolite is a zeolite HY.

5. The method of claim 4 wherein the HY zeolite has a silica to alumina ratio between 2 and 10.

6. The method of claim 1 wherein the crude acetone stream is further treated with a crosslinked acidic polymer resin, and wherein the crosslinked acidic polymer resin is a divinylbenzene-crosslinked sulfonated polystyrene resin.

7. The method of claim 1 wherein the crude acetone stream is 50 wt % or greater acetone.

8. The method of claim 1 wherein the impurity comprises alcohol, epoxide, aldehyde, water, isobutylene, or some combination thereof.

9. The method of claim 1 wherein the purified acetone stream is at least 70 wt % acetone.

10. The method of claim 1 wherein the crude acetone stream comprises about 70-80 wt % acetone, at least 4 wt % methanol, at least 0.2 wt % aldehydes, at least 3 wt % isobutylene oxide, and at least 1 wt % isopropanol.

11. The method of claim 9 wherein the purified acetone stream is at least 80 wt % acetone and less than 0.7 wt % aldehydes, less than 3.5 wt % isobutylene oxide and less than 1.5 wt % isopropanol.

12. The method of claim 1 wherein the purified acetone stream is hydrogenated to produce a crude isopropanol stream.

13. The method of claim 12 wherein the crude isopropanol stream is further purified to produce a purified isopropanol with a purity of at least 99.5 wt %.

14. A method for preparing a purified isopropanol comprising the steps of
 a. feeding a crude acetone stream which comprises acetone and at least one lower boiling impurity to a bed comprising a zeolite to form a treated acetone feed stream that comprises acetone and at least one higher boiling impurity;
 b. distilling the treated acetone stream to remove at least a portion of the higher boiling impurity from the treated acetone stream to produce a purified acetone stream; and
 c. feeding the purified acetone stream to a hydrogenation reactor in a process for making isopropanol to produce a crude isopropanol;
 d. distilling the crude isopropanol stream to remove at least a portion of the remaining impurities to produce a purified isopropanol stream.

15. The method of claim 14 wherein the zeolite is selected from the group consisting of a faujasite, a mordenite, a chavbazite, a clinoptilolite, an erionite, a sihealite, a zeolite A, a zeolite L, a zeolite beta, a zeolite X, a zeolite Y, a zeolite HY, a zeolite ZSM-5, a zeolite MCM-22, a zeolite MCM-41, a zeolite UCB-1 and a zeolite ITQ-2.

16. The method of claim 14 wherein the purified acetone stream is at least 90 wt % acetone.

17. The method of claim 14 wherein the acetone feed stream comprises about 80 wt % acetone, at least 6.5 wt % methanol, at least 0.7 wt % aldehydes, at least 3.5 wt % isobutylene oxide, and at least 1.5 wt % isopropanol, and further wherein the purified acetone stream is about 90 wt % acetone and less than 6.5 wt % methanol, less than 0.7 wt % aldehydes, less than 3.5 wt % isobutylene oxide and less than 1.5 wt % isopropanol, and further wherein the purified isopropanol is at least 99.8 wt % isopropanol.

18. The method of claim 14 wherein the yield of isopropanol is increased by at least 5% when compared to a process of producing isopropanol with an acetone feed stream that has not been treated with a zeolite.

19. A method for preparing a purified isopropanol comprising the steps of
 a. feeding an acetone feed stream which comprises acetone and at least one lower boiling impurity to a bed which comprises a zeolite to form a treated acetone feed stream that comprises acetone and at least one higher boiling impurity;
 b. distilling the treated acetone stream to remove at least a portion of the higher boiling impurity from the treated acetone stream to produce a purified acetone stream having a purity of at least 80%;
 c. feeding the purified acetone stream to a hydrogenation reactor in a process for making isopropanol to produce a crude isopropanol; and
 d. distilling the crude isopropanol stream to remove at least a portion of the remaining impurities to produce a purified isopropanol stream wherein the purified isopropanol has a purity of at least 99.5%.

\* \* \* \* \*